United States Patent [19]

Kuettner et al.

[11] Patent Number: 4,746,729

[45] Date of Patent: May 24, 1988

[54] CARTILAGE-DERIVED LEUKOCYTE ELASTASE-INHIBITOR

[76] Inventors: Klaus E. Kuettner, 426B W. Webster, Chicago, Ill. 60614; Dominique Tripier, D-6239 Eppstein; Dietrich Brocks, D-6200 Wiesbaden 42, both of Fed. Rep. of Germany; Michael T. DiMuzio, 411 S. Sangamon, #4D, Chicago, Ill. 60607

[21] Appl. No.: 890,749

[22] Filed: Jul. 30, 1986

[51] Int. Cl.$^4$ ............... A61K 37/12; A61K 37/02
[52] U.S. Cl. .................... 530/353; 530/395; 530/840; 514/824; 514/825
[58] Field of Search .......... 530/350, 353, 840, 395; 514/2, 8, 12, 13, 14, 21, 825, 824

[56] References Cited

U.S. PATENT DOCUMENTS

| 4,402,872 | 9/1983 | Bohn | 530/395 |
|---|---|---|---|
| 4,404,194 | 9/1983 | Arala-Chaves | 530/350 |
| 4,604,234 | 8/1986 | Fujii et al. | 530/350 |

OTHER PUBLICATIONS

Nakajima et al., *Journ. Biol. Chem.* vol. 254, pp. 4027–4032, 1979.
Hawke et al., *Anal. Biochem.* 120,302–311 (1982).
"Bone Metastasis", Hall, Medical Publishers, 1981, pp. 153–154.

*Primary Examiner*—Delbert R. Phillips
*Assistant Examiner*—Nathan M. Nutter
*Attorney, Agent, or Firm*—Farabow, Garrett and Dunner Finnegan, Henderson

[57] ABSTRACT

A protein or a pharmaceutically acceptable salt thereof. The protein has a molecular weight of 10,000–30,000 Dalton, an isoelectric point greater than 9.5, and an N terminus of the sequence H-Lys-X-Phe-Lys-Val-Asp-Val-Leu-Ala-Ala-Leu-X-Phe-Asn-Ala-, wherein X is an amino acid or a tryptic cleavage product which has the sequence -Gly-Ala-Asn-Ala-Val-Asn-. Methods for the isolation and purification of the protein, compositions containing the protein, and methods for the use of the protein and compositions, are also disclosed.

13 Claims, 4 Drawing Sheets

CARTILAGE-DERIVED LEUKOCYTE ELASTASE-INHIBITOR

BACKGROUND OF THE INVENTION

This invention relates to the new protein, cartelin, which inhibits in vivo and in vitro polymorphonuclear neutrophils (PMN) elastase. More particularly, the invention relates to the use of the new protein in human therapeutics of elastase-mediated tissue injury disease.

In these diseases, metastatic cells or inflammatory cells, such as leucocytes, diffuse in tissue. PMN elastase and its cohort enzymes have a broad specificity towards endogenous substrates, including amorphous elastic and connective tissue components, such as collagen type III, which is the supporting component of lung, blood vessel, and gut connecting tissue, collagen type IV, which is important for the integrity of epithelial and endothelial basement membrane, and fibronectin, which is the cell-adhesion molecule.

These related diseases include pulmonary emphysema, chronic bronchitis, cystic fibrosis, bronchiectasis, adult respiratory distress syndrome, atheriosclerosis, arthritis, psoriasis, vasculitis, glomerulonephritis, consumption coagulopathies associated with gram-negative sepsis, and leukemias. Furthermore, the invasion of tissue during metastasis by neoplastic cells, which is accompanied by collagen cleavage, would be controlled by elastase inhibition.

It has been noticed that some cartilage intrinsically retards the invasion of tumor cells and leucocytes. The resistance is in part due to the avascular nature, the organization, and the composition of the extracellular matrix.

This natural defense against invasion appears to be contained in the extractable cartilage matrix compound named antiinvasive-factor (AIF). See *Bone Metastasis*, G. K. Hall, Medical Publishers, Boston, Mass., 1981, pp. 153–154, incorporated herein by reference. Within this mixture of proteins are a number of protease inhibitors and growth regulatory factors which have been partially purified.

Initial examination of AIF shows that it contains inhibitory activity toward leucocyte-elastase. Therefore, it has been hypothesized that this inhibitor may be an agent responsible for natural protection against metastasis.

In the present invention, AIF was examined for PMN-elastase inhibitory activity using analytical and preparative chromatographic and electrophoretic techniques. The purification steps were monitored by measuring the inhibiting activity with a leucocyte elastase test using a chromogen substrate. A specific PMN-elastase inhibitor was isolated and characterized as a protein of 15,000 daltons on SDS-PAGE with a high cationic character (pI (isoelectric point) greater than 9.5) and a strong hydrophobic behavior.

The amino-terminal-sequence and the sequence of a tryptic peptide showed no homology to other proteins or protease inhibitors or their nucleotide translations. The detected sequences are highly characteristic for the new inhibitors and therefore can be used to synthesize hybridization probes to screen a cDNA mammalian chondrocyte library and clone the gene.

SUMMARY OF THE INVENTION

The invention relates to a protein or a pharmaceutically acceptable salt thereof. The protein of the present invention has a molecular weight of 10,000–30,000 Dalton, an isoelectric point greater than 9.5, and an aminoterminal amino acid sequence of $$\overset{1}{\text{H}}-\text{Lys}-\text{X}-\text{Phe}-\text{Lys}-\overset{5}{\text{Val}}-\text{Asp}-\text{Val}-\text{Leu}-\text{Ala}-$$

$$-\text{Ala}-\overset{10}{\text{Leu}}-\text{X}-\text{Phe}-\text{Asn}-\overset{15}{\text{Ala}}-$$

where X denotes a naturally occurring amino acid or a tryptic cleavage product which has the amino acid sequence -Gly-Ala-Asn-Ala-Val-Asn-.

The protein of this invention forms salts with various inorganic and organic acids, which salts are also within the scope of the invention. Acids from which salts may be prepared include, for example, HCl, HBr, $H_2SO_4$, $H_3PO_4$, methanesulfonic acid, toluenesulfonic acid, maleic acid, fumaric acid, and camphorsulfonic acid. The non-toxic, physiologically acceptable salts are preferred, although other salts are also useful, e.g., in isolating or purifying the product.

The invention also relates to a process for isolating this purified protein, which comprises isolating the protein from cartilage with the aid of a combination of membrane filtration and chromatography.

BRIEF DESCRIPTION OF THE DRAWINGS

The drawings referred to hereafter in the text are briefly described as follows.

DETAILED DESCRIPTION OF THE PREFERRED EMBODIMENTS

The factor from which the new PMN Elastase Inhibitor was isolated is an extracellular extract of bovine nasal septa which are rapidly removed from young animals after slaughtering, thus avoiding contamination of the cartilage with blood. The minced thin pieces are then extracted with saline at low temperature to prevent protease degradation of the inhibitor. The extraction procedure is repeated twice and the extract is purified by separating the high and low molecular weight contaminants by filtration carried out on Amicon Membranes of size exclusion of MW greater than 50,000 (XM-50) and size-exclusion of 1000 (UM-2).

Figure 1:
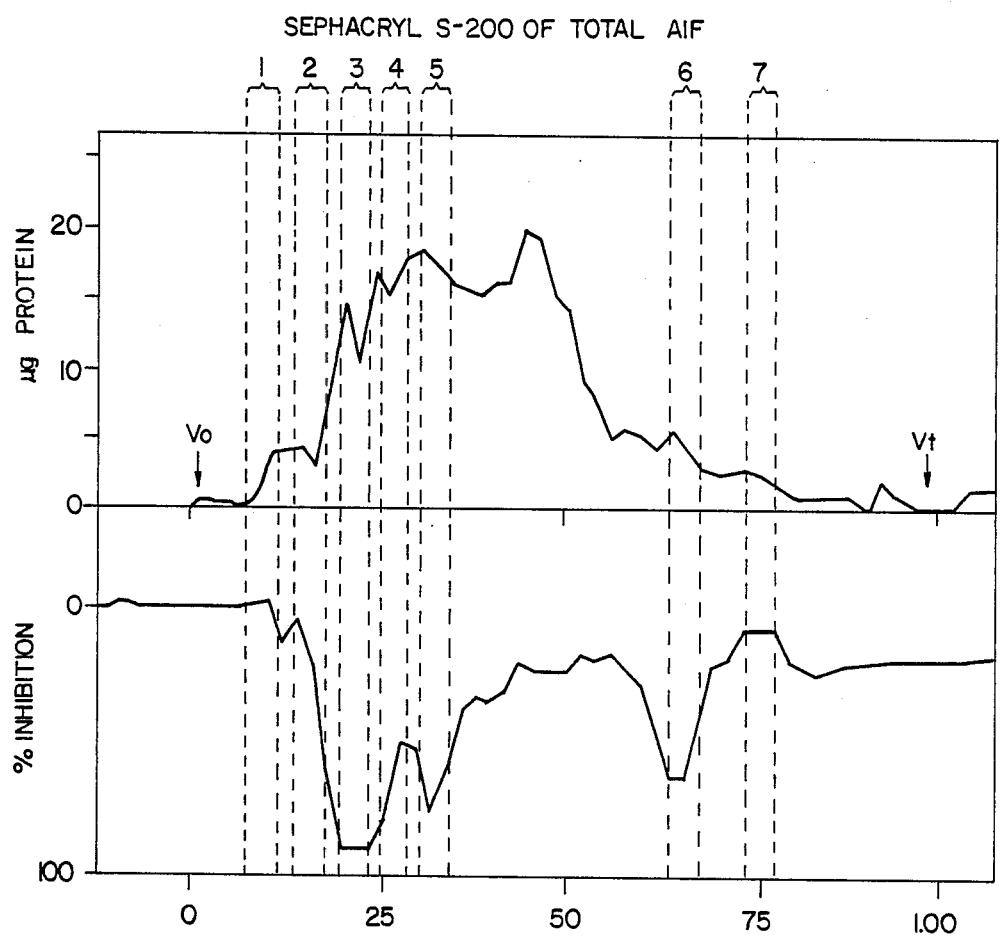
FIG. 1 Elution profile of crude extract of PMN-Elastase Inhibitor on Sephacryl S-200. Inhibition was found in low-molecular range of the elution protein centered on fraction 75.

The new inhibitor moved through the first membrane but was retained by the second. To avoid clogging of the membrane, it was found advantageous to carry out the filtrations in high salt content (3 M NaCl) buffer and then to desalt the crude extract on Sephadex G-25 before fractionation on gel permeation chromatography on Sephacryl S-200, as shown in FIG. 1.

The competitive and concentration dependent PMN-elastase inhibitor was found in the low molecular weight fraction between 10 and 40 KD. The high molecular weight fraction contains some serum albumin (molecular weight : 68 KD), due to the unavoidable contamination of cartilage with blood during biopsis excision.

This small amount of serum albumin was shown to inhibit the PMN-Elastase to a certain extent. This contaminant, which remains as trace material up to the next purification step, is eliminated by cationic exchange chromatography. Each fraction of the Sephacryl S-200 column was assayed for protein content by the dye binding method using bovine serum albumin as the standard (Bio Rad protein assay) and for enzymatic activity.

PMN-Elastase was isolated and purified from human neutrophile as depicted in *Recent Advances In Connective Tissue Research*, 1986, Bukhauser Verlag, Basel, Boston, Stuttgart, C. Arsenis, E. S.-M. A. Thomar, and K. E. Kuettner, pages 63–68, incorporated herein by reference. It has essentially no cathepsin-G activity. The enzyme was tested against its natural substrates, such as type IV collagen, insoluble amorphous elastin, and against the specific synthetic substrate Methoxysuccinyl-L-Alanyl-L-Alanyl-L-Prolyl-L-Valyl-p-nitro-anilide, from which a DMSO stock solution was made. See *The Journal of Biological Chemistry*, Vol. 254, pp. 4027–4032, 1979, K. Nakajima, J. C. Powers, B. M. Ashe, and M. Zimmerman, incorporated herein by reference. Aliquots were diluted with assay buffer for each measurement.

The PMN-Elastase inhibiting fraction was pooled, desalted on Sephadex G-25 with buffer exchange (20 mM phosphate, pH 6.3), and the void volume was absorbed on a carboxy-methylcellulose column (CM Sephadex G-50). By washing with a low salt content buffer (20 mM phosphate, pH 6.3), trace quantities of serum albumin were released from the column. High salt concentration buffers eluted the PMN-elastase inhibitor (2 M NaCl, 20 mM phosphate, pH 6.3).

The column eluent was grossly fractioned (2 ml), and the active fraction pooled, desalted on Sephadex G-85 and lyophilized. The final purification was carried out on HPLC using reversed-phase like material.

The stainless-steel column was filled with a copolymer of divinyl-benzene and styrene with a particle size of 5 microns and a pore size of 300 Å. The material exhibits C-18 reversed phase material property.

This material was shown in previous tests to give high recovery of protein and peptide. This is due to the absence of irreversible absorption sites, which are located on the silica used to manufacture commonly used reversed phase material.

Figure 2:
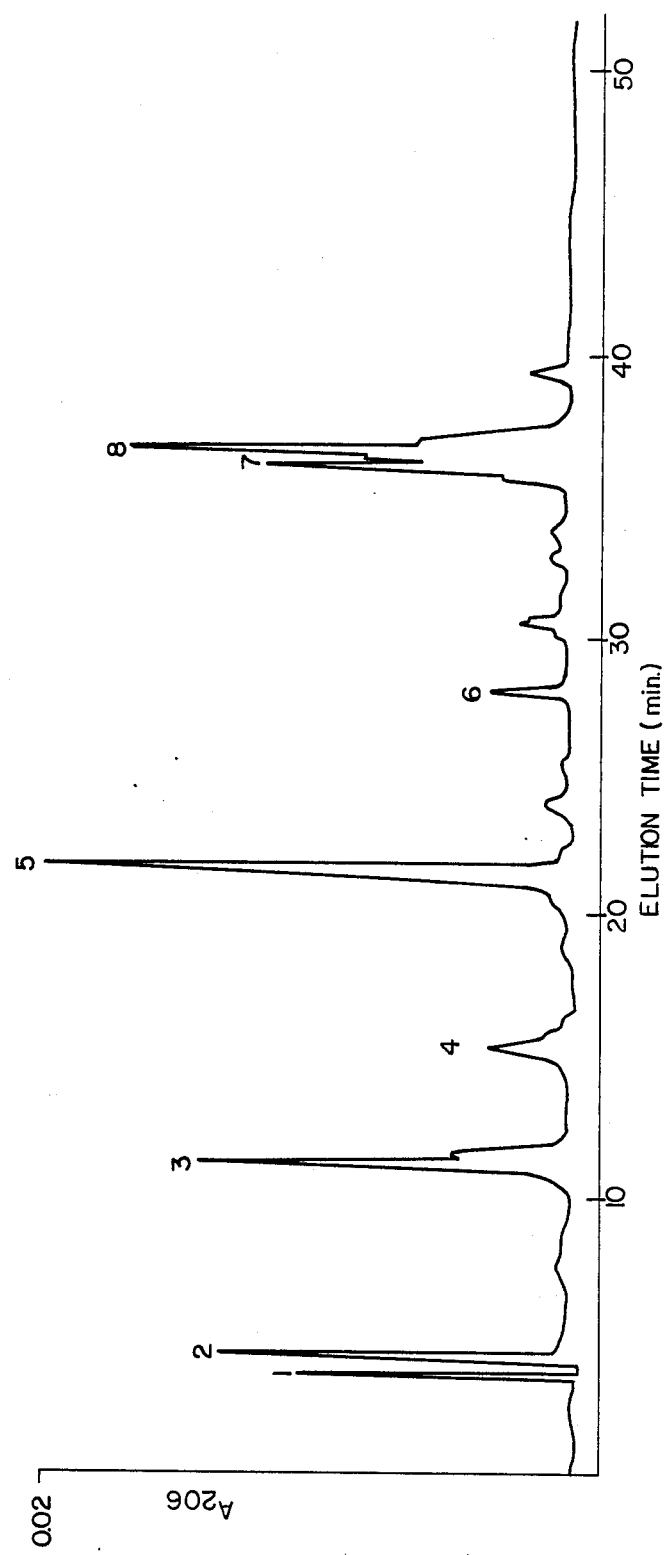
FIG. 2 Reverse-Phase HPLC on PLRP-Column of carboxymethyl-cellulose purified fraction. Each peak was manually collected and assayed for inhibitory activity, which was found in peaks 7 and 8.

Elution of protein or peptide was carried out with linear gradient from 0 to 100% beta. The mobile phase used was the well-known water/acetonitrile/trifluoro acetic acid system, from which peptide and protein are easily recovered. Chromatogram 1, shown in FIG. 2, exhibits the elution pattern of the material purified on the ion-exchange column.

Each peak was manually collected by fractionating at each turning point of the chromatogram and an aliquot was assayed for PMN-Elastase inhibition. PMN-Elastase inhibition activity was found in Peaks 7 and 8 of FIG. 2.

Figure 3:
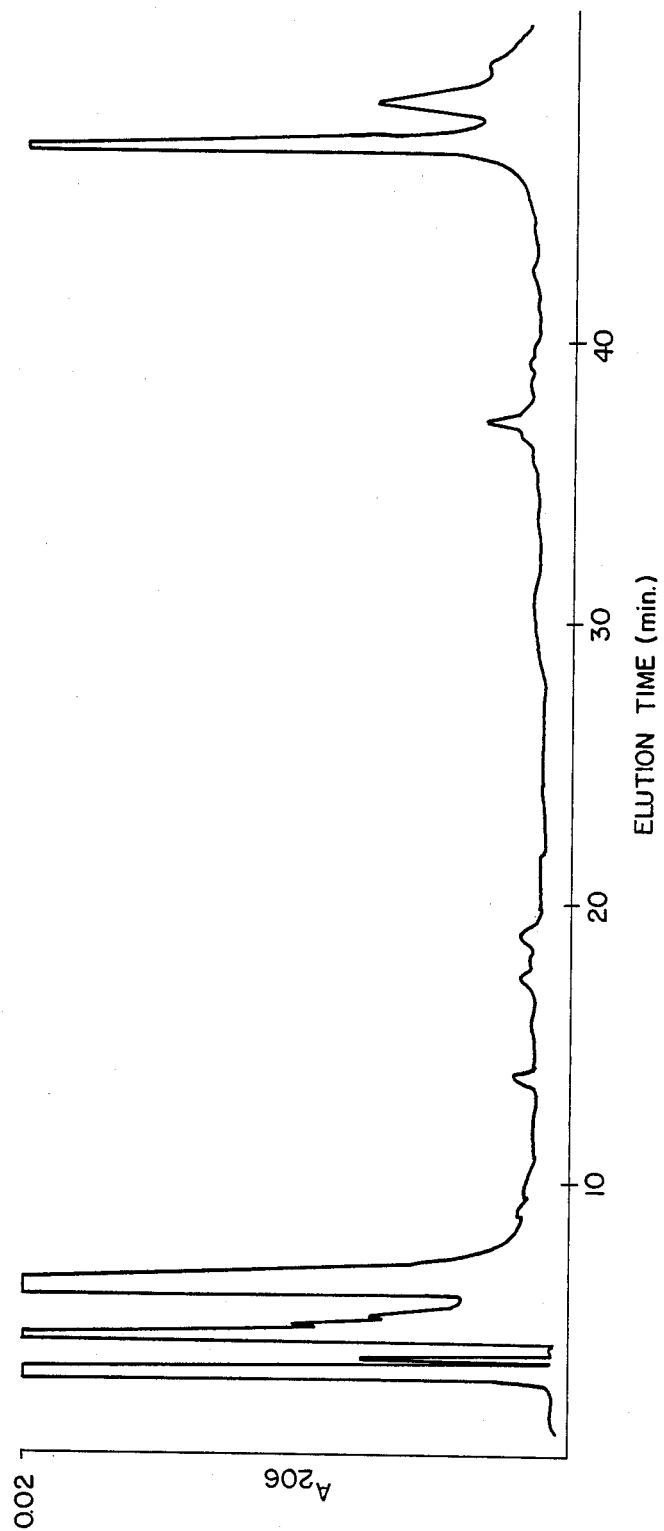
FIG. 3 Rechromatography of Peak 7 of the foregoing chromatogram (FIG. 2). Competitive inhibitory activity was found in peak 7.

Peaks 7 and 8 were rechromatographed, see Chromatogram 2, shown in FIG. 3. The purified substance was submitted to PMN-Elastase inhibition testing and to amino acid and sequence analysis. The purity was tested with SDS-PAGE (17% Acrylamide).

Activity was only found in Peak 7. SDS-PAGE, with three repeated silver-staining procedures, verified that homogeneity of the isolated compound had been obtained.

1/5 aliquot was hydrolysed (106° C., 22 h) in the vapor-phase of 6 N HCl spiked with phenol to prevent degradation of oxidation sensitive amino-acids (Pico-Tag System of Waters Associates). See Millipore Waters Chromatograph Division Application sheet T 85/81505 August 1984, S. A. Cohen, T. L. Tarvin, B. A. Bidlingmeyer, incorporated herein by reference. The hydrolysate was dissolved in the starting buffer of a Beckman Amino Acid Analyser 6300 and analyzed using standard methods employing post column derivatization with orthophthaldialdehyde and fluorescence monitoring (Excitation 356 nm, Emission 450 nm).

This method exhibits a high sensitivity for primary amine but is totally unsensitive for secondary amine. Therefore, histine cannot be analysed and thus the number of histidine-residues of the new inhibitor is not presently determinable.

The amino acid analysis of the PMP-Elastase Inhibitor, which for obvious reasons can vary in a 10–15% range, is as follows:

| AMINO ACID ANALYSIS OF THE CARTILAGE-DERIVED 15,000 DALTON ELASTASE INHIBITOR | |
|---|---|
| RESIDUE | #/MOLECULE |
| Cys | 6.8 |
| Asp | 16.8 |
| Thr | 7.6 |
| Ser | 5.8 |
| Glu | 10.4 |
| Gly | 7.8 |
| Ala | 10.4 |
| Val | 4.1 |
| Met | 1.0 |
| Ile | 2.0 |
| Leu | 12.2 |
| Tyr | 3.8 |
| Phe | 5.0 |
| His | — |
| Lys | 37.4 |
| Arg | 16.6 |

Sequence analyses were performed on a Beckman 890 M Sequencer using the revision C of the supplier's programs. The released Phenylthiohydantoin-amino acids (PTH) were identified with HPLC analysis on a Waters system fitted with an Altex Ultrasphere ODS column (4.6×250 m) filled with reversed phase material (C-18) of a particle size of 5 microns.

The step gradient and the buffers used were basically, with minor adaptations, those described in *And. Biochem.* 120, 302–311, (1982) D. Hawke, Pan-Mian Yuan, J. E. Shilvey, incorporated herein by reference. Diethylphthalate was added to the PTH after the conversion, as an internal standard to monitor the manual transfer of the PTH from the sequencer to the HPLC identification system. U.V. monitoring was carried out at 265 nm.

The aminoterminal sequence of the new inhibitor is:

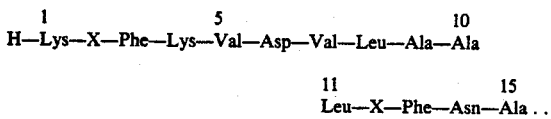

in which X is any naturally occurring amino acid but preferentially is a residue which can be the site of glycosylation, such as L-serine, L-threonine, L-glutamine, L-asparagine, or any posttranslationally modified amino-acid, such as trimethyllysine or gamma-carboxyglutamic acid.

Difficulty in identifying X can arise from the presence at this position of the sequence of a half-cystine which will not be released from the peptide at this degradation step.

Figure 4:
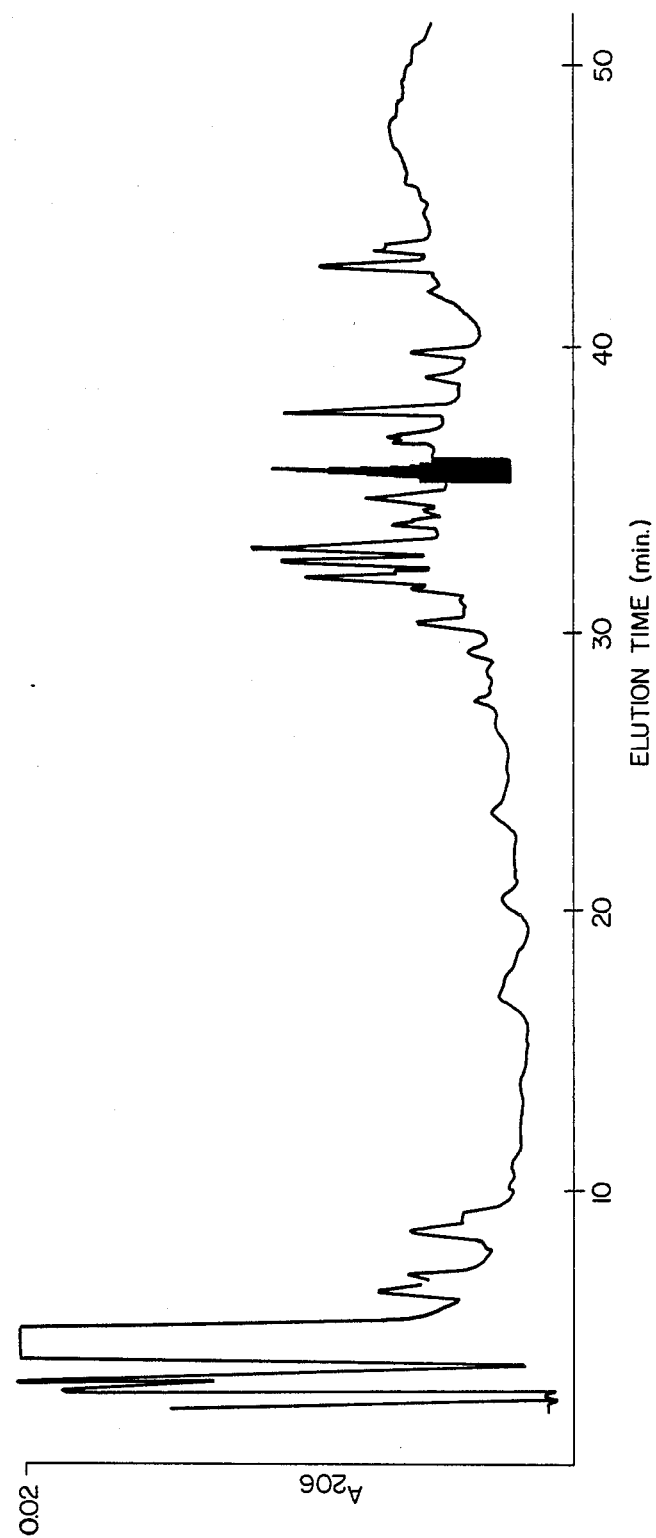
FIG. 4 Reverse-Phase HPLC of tryptic digestion of active fraction. The entire digest was injected on the column and peak manually collected. The cross-hatched peak was sequenced.

Approximately 20 micrograms PMN-Elastase-Inhibitor was engaged in a tryptic digestion using 0.2 micrograms TPCK-Trypsin. The entire digest was injected on HPLC-column and eluted with a swallow sloped gradient to give the chromatogram 3, shown in FIG. 4. Peaks were manually collected and the cross-hatched peak was directly sequenced to give the following result:

Gly-Ala-Asn-Ala-Val-Asn ...

The polypeptides according to the invention can be used parenterally, for example, subcutaneously or intravenously, or via mucous membranes, for example, nasally or transdermally.

The dosage for parenteral administration is 0.01–50 mg/m² of body surface/day, depending on the type of disease. In serious cases, it can also be increased, since no toxic properties have yet been observed.

In particularly serious cases, several administrations per week over a period of several weeks are recommended. As a result of the particular absorption properties, dosages for nasal administration must be correspondingly higher.

For subcutaneous, intravenous, or nasal administration, the compounds according to the invention or physiologically acceptable salts thereof are converted into a solution, suspension, or emulsion, if desired, with the conventional substances, such as solubilizing agents, emulsifiers, or other auxiliaries.

Examples of possible solvents for the novel active compounds and the corresponding physiologically acceptable salts are: water, physiological saline solutions or alcohols, for example, ethanol, propanediol, or glycerol, as well as sugar solutions, such as glucose or mannitol solutions, or a mixture of the various solvents mentioned.

Parenteral administration can also be effected, for example, with external or implanted metering devices, such as, for example, automatic pumps, or in the form of a continuous drip. In this case, it is advantageous to add compounds that stabilize against denaturation, such as are known, for example, from European patent application No. 18,609, which is incorporated herein by reference.

The compounds according to the invention can also be administered in the form of a medicament with a delayed release action. In the case of injection solutions, such a delayed release action can be achieved, for example, by dissolving or suspending the medicament in an oily vehicle, adding macromolecules which increase the viscosity and which delay the diffusion of the dissolved medicaments, absorbing the medicament onto suitable carrier molecules, for example aluminum hydroxide, or using crystal suspensions.

On the basis of the analysed amino acid sequences, probes can be constructed which will hybridize with the gene for cartelin when screening a genomic or cDNA gene library with these probes under less stringent conditions. Thereafter, screening the positive clones with the same or a different probe under more stringent conditions will yield a small number of clones containing the complete DNA coding for cartelin or a substantial part thereof. For the latter case, a new screening with this partial DNA sequence will give the complete DNA sequence.

```
Probe 1:    Phe—Lys—Val—Asp—Val
            TTC AAA GTA GAC GT
              T   G   C   T
                          G
                          T
            14 mer probe, 32 times degenerated
Probe 2:    Asn—Ala—Val—Asn
            AAC GCA GTA AA
              T   C   C
                  G   G
                  T   T
            14 mer probe, 32 times degenerated
Probe 3:    Phe—Lys—Val—Asp—Val—Leu
            TTC AAA GTI GAC GTI CTI
              T   G
            18 mer, 8 times degenerated.
```

The "degeneration" can further be reduced by considering the known code usage of mammals.

Variations of cartelin can be constructed by making a synthetic gene, e.g. by the phosphite method, in which any desired amino acid can be exchanged for any given amino acid. Thus, in the gene for the aminoterminal amino acid sequence, X can be a codon for any genetically codable amino acid, preferably for Ser, Thr, Gln, Cys or Asn, but especially for Ser.

Likewise, deletions or insertions of genetically codable amino acids are possible.

It is to be understood that the application of the teachings of the present invention to a specific problem or environment will be within the capabilities of one having ordinary skill in the art in light of the teachings contained herein. The following examples are representative of the invention but do not in any way constitute limitations thereof.

EXAMPLE 1

Preparation of crude extract

Slices of fresh, hyaline cartilage prepared from the nasal septa of 18-month-old bovines were extracted with 5 volumes (weight/volume) of saline (1 M NaCl, 0.05 M sodium acetate, pH 5.8; 24 h; 4° C.). The extract was decanted from the tissues, filtered through two gauzes, adjusted to 3 M NaCl, by adding NaCl, and purified using Amicon filtration on XM-50 membrane at 20 psi and 4° C. The ultrafiltrate was pressed on a UM-2 Membrane at 40 psi and 4° C. The UM-2 residue was washed twice with saline (0.5 M NaCl, 20 mM Tris HCl, pH 7.3).

EXAMPLE 2

Gel Filtration Chromatography

The crude extract was concentrated on a Sephadex G-25 (1×10 cm) column (0.5 NaCl, 20 mM Tris HCl, pH 7.3) and the void volume peak chromatographed on an analytical (1×150 cm) column of Sephacryl S-200. Each fraction (1 ml) of the eluent was assayed for protein (Bio-Rad Protein Assay) and PMN-Elastase inhibitory activity and the active fractions of low molecular weight (10 to 40 KD) were pooled.

EXAMPLE 3

Cationic exchange chromatography

Buffer-exchange (20 mM phosphate, pH 6.3) was performed on a Sephadex G-25 (1×10 cm) column and the void column peak pumped on a short carboxy-methyl-cellulose (CM-Sephadex G-50) column (1.5×20 cm). The column was washed with three column volumes of phosphate buffer and eluted with saline (1 M NaCl, 20 mM phosphate, pH 6.3). The fractionated eluent (3 ml) was assayed for protein content, and enzymatic activity. The active fractions were pooled and desalted on Sephadex G-25 using 20 mM phosphate pH 6.3.

EXAMPLE 4

Inhibition Assays 30 microliters (2.5–15 micrograms protein/ml) of PMN-Elastase was poured into a 96 well-plate, and 70 microliters of sample were added and incubated for 30 minutes at 30° C. After addition of 100 microliters substrate solution (methoxy-succinyl-L-Alanyl-L-Alanyl-L-Prolyl-L-Valyl-p-nitroanilide) in DMSO, dilution to 3 mM was effected with a buffer solution of 20 mM Tris and 500 mM NaCl at pH 7.3 (final DMSO concentration 10%). The reaction was followed by monitoring the 405 nm absorption of the cleaved paranitroanlide and comparison to the time-zero value. By varying the enzyme quantities, semiquantitative relationships were obtained.

EXAMPLE 5

HPLC Analysis

HPLC was carried out on a Waters Associates System fitted with 4.6×250 mm column filled with PLRP-material of 5 microns particle size and 300 A pore size (Polymer Labs LTS Amherst, Mass.). The column effluent (1 ml m$^{-1}$) was monitored at 216 nm. The mobile phase consisted of:

A: 0.1% trifluoroacetic acid (TFA) in 10% acetonitrile/water.
B: 0.1% TFA in 90% acetonitrile/water. The gradient was linear with a slope of 1% min.

EXAMPLE 6

Tryptic Digestion

The solution of PMN-elastase inhibitor in 100 microliters 0.2 N-Methylmorpholine-acetate buffer, pH 8.1, was mixed with 10 microliters buffer containing 0.2 micrograms Tos-Phe-CH$_2$Cl treated trypsin (Merck) and incubated at 37° C. for 5 hours. The reaction was stopped by freezing. The tryptic peptides were separated on HPLC using a gradient of 0% to 100% beta with a slope of 0.5% min$^{-1}$.

It will be apparent to those skilled in the art that various modifications and variations can be made to the processes and products of the present invention. Thus, it is intended that the present invention cover the modifications and variations of this invention, provided they come within the scope of the appended claims and their equivalents.

We claim:

1. A substantially purfied protein or a pharmaceutically acceptable salt thereof, said protein having a molecular weight of 10,000–30,000 Dalton, an isoelectric point greater than 9.5, and an aminoterminal amino acid sequence of H—Lys—X—Phe—Lys—Val—Asp—Val—Leu—Ala—

—Ala—Leu—X—Phe—Asn—Ala— wherein each X may be identical or different and each denotes a naturally occurring amino acid or a tryptic cleavage product that has the amino acid sequence -Gly-Ala-Asn-Ala-Val-Asn-.

2. A protein or a pharmaceutically acceptable salt thereof as claimed in claim 1, which has a molecular weight of 12,000–20,000 Dalton.

3. A protein or a pharmaceutically acceptable salt thereof as claimed in claim 1, which has a molecular weight of 14,000–18,000 Dalton.

4. A protein or a pharmaceutically acceptable salt thereof as claimed in claim 1, which has a molecular weight of approximately 15,000 Dalton.

5. A protein or a pharmaceutically acceptable salt thereof as claimed in claim 1, wherein the radical X is selected from the group consisting of Ser, Thr, Glu, Asn, and Cys.

6. A protein or a pharmaceutically acceptable salt thereof as claimed in claim 5, in which X denotes Ser.

7. A protein or a pharmaceutically acceptable salt thereof as claimed in claim 5, in which either or both of the radicals X are glycosylated.

8. A protein or a pharmaceutically acceptable salt thereof as claimed in claim 1, the amino acid analysis of which is:

| Cys | 6.8 ± 15% |
|---|---|
| Asp | 16.8 ± 15% |
| Thr | 7.6 ± 15% |
| Ser | 5.8 ± 15% |
| Glu | 10.4 ± 15% |
| Gly | 7.8 ± 15% |
| Ala | 10.4 ± 15% |
| Val | 4.1 ± 15% |
| Met | 1.0 ± 15% |
| Ile | 2.0 ± 15% |
| Leu | 12.2 ± 15% |
| Tyr | 3.8 ± 15% |
| Phe | 5.0 ± 15% |
| Lys | 37.4 ± 15% |
| Arg | 16.6 ± 15% |

9. A protein or a pharmaceutically accepatable salt thereof as claimed in claim 1, the amino acid analysis of which is:

| Cys | 6.8 ± 10% |
|---|---|
| Asp | 16.8 ± 10% |
| Thr | 7.6 ± 10% |
| Ser | 5.8 ± 10% |
| Glu | 10.4 ± 10% |
| Gly | 7.8 ± 10% |
| Ala | 10.4 ± 10% |
| Val | 4.1 ± 10% |
| Met | 1.0 ± 10% |
| Ile | 2.0 ± 10% |

| | -continued |
|---|---|
| Leu | 12.2 ± 10% |
| Tyr | 3.8 ± 10% |
| Phe | 5.0 ± 10% |
| Lys | 37.4 ± 10% |
| Arg | 16.6 ± 10% |

10. A pharmaceutical composition comprising an effective amount of a protein or a pharmaceutically acceptable salt thereof as claimed in claim 1 and a pharmaceutically acceptable carrier.

11. A method of inhibiting PMN elastase which comprises the step of adminsitering to a hos in need of such treatment an effective amount of a protein or a pharmaceutically accepatable salt thereof as claimed in claim 1.

12. An enzymatic peptide cleavage product of a protein or a pharmaceutically acceptable salt thereof as claimed in claim 1 consisting of 6 or more amino acids.

13. A method of treating pulmonary emphysema, chronic bronchitis, cystic fibrosis, bronchiectasis, adult respiratory distress syndrome, atherosclerosis, arthritis, psoriasis, vasculitis, glomerulonephritis, consumption coagulopathies associated with gram-negative sepsis, and leukemias, compring the step of administering to an affected host an effective amount of a protein or pharmaceutically acceptable salt thereof as claimed in claim 1.

* * * * *

UNITED STATES PATENT AND TRADEMARK OFFICE
CERTIFICATE OF CORRECTION

PATENT NO. : 4,746,729

DATED : May 24, 1988

INVENTOR(S) : Klaus E. Kuettner et al.

It is certified that error appears in the above-identified patent and that said Letters Patent is hereby corrected as shown below:

Claim 11, Column 9, Line 15, change "adminsitering" to --administering--.

Claim 11, Column 10, Line 2, change "accepatable " to --acceptable--.

Signed and Sealed this

Fourteenth Day of March, 1989

Attest:

DONALD J. QUIGG

*Attesting Officer*

*Commissioner of Patents and Trademarks*